(12) United States Patent
Freyberg et al.

(10) Patent No.: US 7,008,773 B1
(45) Date of Patent: Mar. 7, 2006

(54) METHOD FOR IDENTIFYING ACTIVE ANTI APOPTOSIS COMPOUNDS

(75) Inventors: Mark A. Freyberg, Darmstadt (DE); Peter Friedl, Gross-Umstadt (DE); Dirk Kaiser, Eppertshausen (DE)

(73) Assignee: CytoTools GmbH, Darmstadt (DE)

( * ) Notice: Subject to any disclaimer, the term of this patent is extended or adjusted under 35 U.S.C. 154(b) by 191 days.

(21) Appl. No.: 10/129,295

(22) PCT Filed: Nov. 2, 2000

(86) PCT No.: PCT/EP00/10806

§ 371 (c)(1),
(2), (4) Date: Aug. 29, 2002

(87) PCT Pub. No.: WO01/33218

PCT Pub. Date: May 10, 2001

(30) Foreign Application Priority Data

Nov. 3, 1999 (DE) ................................ 199 52 960

(51) Int. Cl.
*C12Q 1/68* (2006.01)
(52) U.S. Cl. ...................................... 435/7.1; 435/7.21
(58) Field of Classification Search ................ 445/7.1, 445/7.21, 287.1
See application file for complete search history.

(56) References Cited

U.S. PATENT DOCUMENTS 6,191,269 B1 * 2/2001 Pollock et al.
6,562,797 B1 * 5/2003 Dixit et al.

FOREIGN PATENT DOCUMENTS

EP          903 149 A1     3/1999
WO          WO 99/40940    8/1999

OTHER PUBLICATIONS

Kuntz, Structure-based strategies for drug design and discovery. Science. 1992 257(5073):1078-1082.*

"Thrombospondin Modulates $\alpha_v\beta_3$ Function Through Integrin-Associated Protein", Gao et al., The Journal of Cell Biology, vol. 135, No. 2, Oct. 1996, pp. 533-544.

"CD47 Ligation Induces Caspase-Independent Cell Death in Chronic Lymphocytic Leukemia", Mateo et al., Nature Medicine, vol. 5, No. 11, Nov. 1999, pp. 1277-1284.

"Flow Patterns and Spatial Distribution of Atherosclerotic Lesions in Human Coronary Arteries", Asakura et al., McGill University Medical Clinic, Montreal General Hospital, Nov. 8, 1989, pp. 1045-1066.

"Use of fluo-3 to Measure Cytosolic $Ca^{2+}$ in Platelets and Neutrophils", Merritt et al., Biochem J. (1990) 269, pp. 513-519.

"Features of Apoptotic Cells Measured by Flow Cytometry", Darzynkiewicz et al., Cytometry 13 (1992). pp. 795-808.

"Optimal Detection of Apoptosis by Flow Cytometry Depends on Cell Morphology", Zamai et al., Cytometry 14 (1993), pp. 891-897.

"A 50-kDa Integrin-associated Protein is Required for Integrin-Regulated Calcium Entry in Endothelial Cells", Schwartz, et al., The Journal of Biological Chemistry, vol. 268, No. 27, Sep. 25, 1993, pp. 19931-19934.

"Structrual and Functional Aspects of RGD-Containing Cyclic Pentapeptides as Highly Potent and Selective Integrin $\alpha_v\beta_3$ Antagonists", Haubner et al., Journal of the American Chemical Society, 1996, pp. 7461-7472.

* cited by examiner

*Primary Examiner*—Christina Chan
*Assistant Examiner*—Maher Haddad
(74) *Attorney, Agent, or Firm*—Marshall, Gerstein & Borun LLP (57) ABSTRACT

The invention relates to a method for identifying substances with antiapoptotic activity, where
i) cells which express both IAP and the integrin $\alpha_v\beta_3$ are cultured,
ii) the cells are caused to produce an apoptosis-inducing substance, and/or a substance or substances which induces/induce apoptosis is/are added,
iii) the test substance is added, and
iv) the apoptosis rate is measured, and to the substances which can be identified with the method.

6 Claims, 6 Drawing Sheets

METHOD FOR IDENTIFYING ACTIVE ANTI APOPTOSIS COMPOUNDS

The invention relates to a method for identifying substances with antiapoptotic activity and to the substances identified thereby. The invention further relates to pharmaceutical preparations which comprise such substances, and to their use for the treatment of vascular disorders.

Arteriosclerosis ("arterial calcification") is the most important and commonest pathological change in the arteries. It is associated with a change in the vessel content and with lesions of the endothelium (of the endothelial cells) and, caused thereby, metabolic and cellular reactions of the vessel wall. Disturbances of arterial blood flow are the commonest cause of death in industrialized countries (about 50%). The basis thereof in most cases is arteriosclerosis.

The efficacy of agents currently employed against coronary heart disease is based essentially on reducing the myocardial oxygen consumption and adjusting the reduced coronary blood flow. These agents additionally bring about dilation of the coronary arteries. On the other hand, it is scarcely possible by medication to increase the coronary blood flow in cases of arteriosclerotic coronary stenosis because the diseased vessels can no longer be dilated. All medicaments act only in a very late stage of the disorder. No agents are yet known to be able to treat the cause of the disorder directly or to be suitable for early diagnosis. In the absence of an effective possibility of early diagnosis, most patients are treated only after a mild cardial infarction. In the advanced stage, usually a surgical operation (e.g. bypass) is the only option left.

The inner walls of all blood vessels are lined by endothelial cells. They are involved in the regulation of various physiological processes such as, for example, the regulation of blood pressure and the degeneration and regeneration of vessels. A large number of pathological situations is associated with dysfunction of endothelial cells, for example the focal development of arteriosclerosis.

Apoptosis (synonym: programmed cell death) is an irreversible process and cannot be stopped. Accordingly, an apoptotic cell inevitably dies.

European patent application EP-A-0 903 149 describes a method for identifying apoptosis-inducing substances in immune cells. It showed that substances which bind to the integrin-associated protein (IAP or CD 47) on the surface of immune cells may have the ability to induce apoptosis. The mechanism of action was not described.

It has already been proposed that IAP is involved in the formation of a specific calcium channel (Schwartz, M. A. et al., The Journal of Biological Chemistry, 268:27, 19931–19934). A role of this hypothetical calcium channel in the induction of apoptosis was not mentioned.

Arteriosclerotic lesions form more frequently at bifurcations (forks) in the vascular system than in unbranched regions of the blood vessels. It has already been possible to observe apoptotic endothelial cells in the region of these lesions. It is suggested that apoptotic endothelial cells are involved in the development of arteriosclerosis [Asakura, T., Karino, T., *Circulation Research*, 66, 1045–1066 (1990)].

No agents are currently known for the prevention or therapeutic treatment of the occurrence of apoptosis in endothelial cells of the vascular system.

The present invention is therefore based on the object of providing a method with which it is possible to find substances which inhibit apoptosis in endothelial cells. This method is simple to operate and reliable and cost-effective to carry out. The substances identified in this way are to be employed as ingredients of pharmaceutical preparations for the treatment of conditions in which an inhibition of apoptosis is indicated, in particular of vascular disorders, particularly preferably of arteriosclerosis.

This object is achieved by a method for identifying apoptosis-inhibiting substances and substances with anti-apoptotic activity, wherein cells which express both IAP and the integrin $\alpha_v\beta_3$ are cultivated, and/or the cells are caused to produce an apoptosis-inducing substance and/or a substance(s) which induces/induce apoptosis is/are added, a test substance is added and the apoptosis rate is measured. The invention likewise encompasses substances which can be identified by the claimed method, pharmaceutical preparations which comprise such a substance as active ingredient, and the use of this pharmaceutical preparation for the treatment of vascular disorders, in particular for the treatment of arteriosclerosis. The invention further encompasses the use of substances which have been identified with the aid of the method of the invention for treating vascular disorders, in particular for treating arteriosclerosis.

The inventors have surprisingly shown that the simultaneous binding of thrombospondin-1 (TSP-1) to IAP and integrin $\alpha_v\beta_3$ induces apoptosis in endothelial cells. It has additionally been possible to show, surprisingly, that TSP-1 is produced by the endothelial cells themselves, and thus the apoptosis is self-induced or spontaneous. These investigations were carried out in conventional, static cell cultures. These are distinguished by the absence of any flows in the cell culture medium. However, it was unexpectedly possible to show that endothelial cells produce no TSP-1 in a perfusion culture, i.e. under conditions where the cells are confronted by a flowing cell culture medium, and apoptosis occurs to only a very small extent or not at all in this cell culture.

Supplementation of fresh medium with TSP-1 causes an increase in spontaneous apoptosis in statically cultivated endothelial cells. This increase corresponds approximately to the effect of statically conditioned medium (i.e. medium which has previously been used for the cultivation of HUVEC in static culture) (table 1). This shows that statically conditioned medium has the ability to induce apoptosis via a mediator such as TSP-1.

The term "conditioned" medium means herein a cell culture medium which has previously been used for cultivating other cells. This medium is distinguished by having dissolved in it soluble mediators, e.g. growth factors, hormones etc., which are produced by cells during their cultivation.

It was possible to show by use of an anti-TSP-1 antibody which binds to and thus neutralizes TSP-1 that TSP-1 is the mediator of the apoptosis of endothelial cells. The effect of added TSP-1 can be suppressed, just like the effect of statically conditioned medium, by addition of a polyclonal antiserum against TSP-1 and by addition of a monoclonal anti-TSP-1 antibody (table 1).

TABLE 1

| Culture conditions | Culture medium (24 h) | Apoptosis rate (%) |
|---|---|---|
| Static | Fresh medium (a) | 0.9 ± 0.1 |
| Static | Conditioned medium (b) | 3.0 ± 0.2 |
| Static | Conditioned + anti-TSP 1 (c) | 0.1 ± 0.1 |
| Static | Fresh + TSP 1 (e) | 3.0 ± 0.4 |
| Static | Fresh + anti-TSP 1 (d) | 0.2 ± 0.1 |
| Static | Fresh + TSP I + anti-TSP 1 (f) | 0.2 ± 0.1 |
| Static | Fresh + mAb TSP 1 (g) | 0.4 ± 0.1 |

The apoptosis rate (%) was determined as shown in example 5. The letters (a) to (g) relate to the investigations presented in example 9 and to the specific experimental conditions chosen therein (see example 9).

Figure 1:
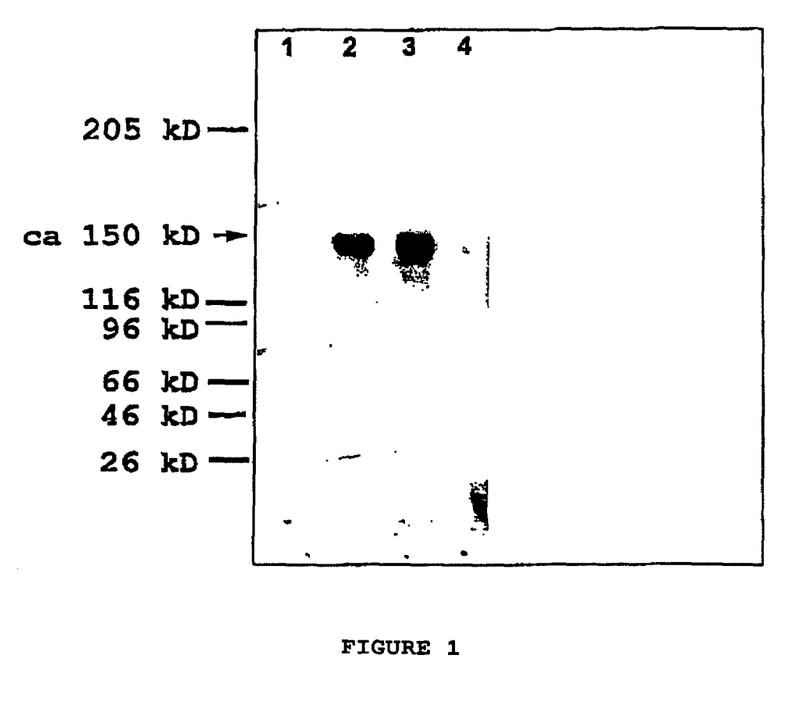
FIG. 1 shows the detection of thrombospondin in the supernatant of endothelial cells (HUVEC) cultivated under serum-free conditions. Western blot analysis with anti-thrombospondin antibodies. Row 1: serum-free medium; row 2: serum-free medium, statically conditioned for 4 days; row 3: 500 ng of TSP-1; row 4: serum-free medium, dynamically conditioned for 3 days.
Figure 2:
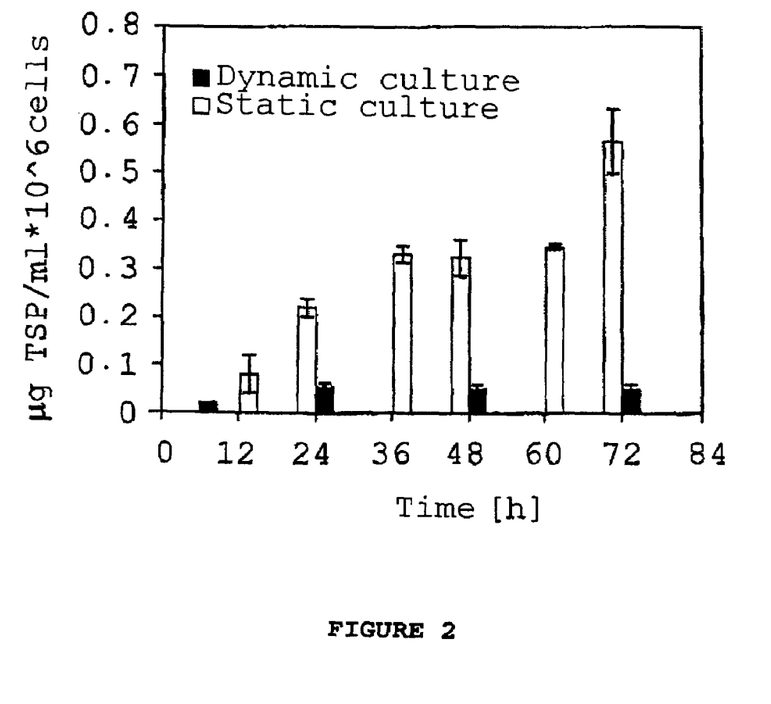
FIG. 2 shows the quantitative detection of the secreted TSP-1 in the supernatant of statically and dynamically cultivated endothelial cells (HUVEC).

It was additionally shown qualitatively by Western blot investigations that TSP-1 is secreted only by statically cultivated endothelial cells (FIG. 1). The secretion rates were determined for dynamic and static postconfluent cultures (FIG. 2). The results showed that induction of apoptosis can be controlled via the TSP-1 secretion rate.

The term "static cell culture (conditions)" means here a cultivation of cells under conditions with which invariable, i.e. consistently directed, laminar flows do not occur in the cell culture medium surrounding the cells. The "static cell culture conditions" in this sense used herein thus include cell culture conditions under which turbulent or variable laminar flows, that is to say, for example, those with changing directions of flow or even with reversal of flow, occur. The term "dynamic cell culture (conditions)" means here cell culture conditions with which only consistently directed, laminar flow conditions prevail in the cell culture medium, i.e. cell culture conditions like those which can be achieved in the prior art for example with the aid of a so-called perfusion culture. It is clear that the conditions of idealized physical fluid mechanics are not attained either in the blood vessel system, i.e. in the in vivo situation, or under cell culture conditions. The flow conditions described herein are thus those which can approximately be attained, and are used, generally in cell culture experiments in the prior art.

The shear stresses thus acting on the cultivated cells vary with the flow conditions. A consistently directed laminar flow results in a shear stress which is greater than 0.001 $dyn/cm^2$ and whose vector sum is greater than under variable flow conditions with changing directions of flow. Static cell culture (conditions) are distinguished by a distinctly smaller (<0.001 $dyn/cm^2$) or absolutely no stress. Dynamic cell cultures show shear stresses of >0.001 $dyn/cm^2$ or a Reynolds number of >0.1. Turbulent flows may occur at Reynolds numbers of >200 (−1000) (depending on the geometry of the flow chamber) and, like static or variable flow conditions, no longer have a protective character in relation to induction of apoptosis.

However, surprisingly, addition of TSP-1 to a perfusion culture generally has no effect on apoptosis. This shows that apoptosis depends not only on the occurrence of TSP-1 in the bloodstream but, on the contrary, also on the occurrence or accessibility of specific receptors on the surface of the cells. It was surprisingly possible to show in this connection that the integrin $\alpha_v\beta_3$ receptor is detectable on statically and dynamically cultivated cells, whereas the IAP receptor is expressed in detectable quantities only in static culture.

It is known that TSP-1 binds to the integrin $\alpha_v\beta_3$. The binding of TSP-1 to the $\alpha_v\beta_3$ integrin is mediated by an RGD sequence motif. A potent agonist of RGD-mediated binding, a cyclic Arg-Gly-Asp-(D-Phe)-Val peptide (cyclic RGD peptide) (supplied by Merck), was therefore added to postconfluent endothelial cells. However, this unexpectedly had no effect on the apoptosis rate. This showed that binding of TSP-1 to the integrin $\alpha_v\beta_3$ at least does not on its own lead to apoptosis induction (table 2).

TABLE 2

| Culture medium (48 h) | Apoptosis rate (%) |
| --- | --- |
| Fresh medium (control) | 1.5 ± 0.2 |
| Conditioned medium | 6.4 ± 0.5 |

TABLE 2-continued

| Culture medium (48 h) | Apoptosis rate (%) |
| --- | --- |
| Fresh + TSP1 | 6.9 ± 1.2 |
| Fresh + active RGD | 1.2 ± 0.5 |
| Fresh + inactive RGD | 1.0 ± 0.4 |
| Fresh + CBD | 2.0 ± 0.2 |
| Fresh + CBD + active RGD | 7.0 ± 0.6 |
| Fresh + CBD + inactive RGD | 1.7 ± 0.6 |
| Fresh + CBD + active RGD + anti-TSP1 | 6.3 ± 1.3 |

The apoptosis rate was determined as shown in example 5. Cultivation in fresh medium serves as control and shows a spontaneous apoptosis rate in static cell culture. Conditioned medium has previously been incubated with endothelial cells for 48 to 72 hours, so that it contained the factors secreted by the endothelial cells. The apoptosis rate caused by the conditioned medium was at the same level as with fresh medium+TSP-1, which showed that one or more mediator(s) of apoptosis must have been present in this conditioned medium. The preparation of conditioned medium is explained in example 4.

Another possible interaction of TSP-1 with a receptor on endothelial cells is the binding to IAP via the C-terminal cell binding domain (CBD). The C-terminal cell binding domain (CBD) is a TSP-1 domain which interacts specifically with IAP. A truncated TSP-1 which consists only of this C-terminal cell binding domain is marketed by Bachem as CBD peptide. Addition of the CBD peptide did not lead to an increase in the apoptosis rate (table 2). Simultaneous addition of the CBD peptide and the cyclic RGD peptide did, however, surprisingly lead to a marked increase in the apoptosis rate (table 2), which was at a similar level to the increase in the apoptosis rate by addition of TSP-1. It follows from this that only simultaneous binding to IAP and the integrin $\alpha_v\beta_3$ is effective for apoptosis.

Substitution of an inactive RGD peptide for one of the other two peptides causes the effect to disappear again. Giving anti-TSP-1 antiserum simultaneously with the two active peptides has no effect on the increase in the apoptosis rate (table 2). This shows that the production of TSP-1 during the incubation has no effect. It was thus possible to show, surprisingly, that the activity of TSP-1 for inducing spontaneous apoptosis is mediated by simultaneous binding to IAP and $\alpha_v\beta_3$.

Figure 3:
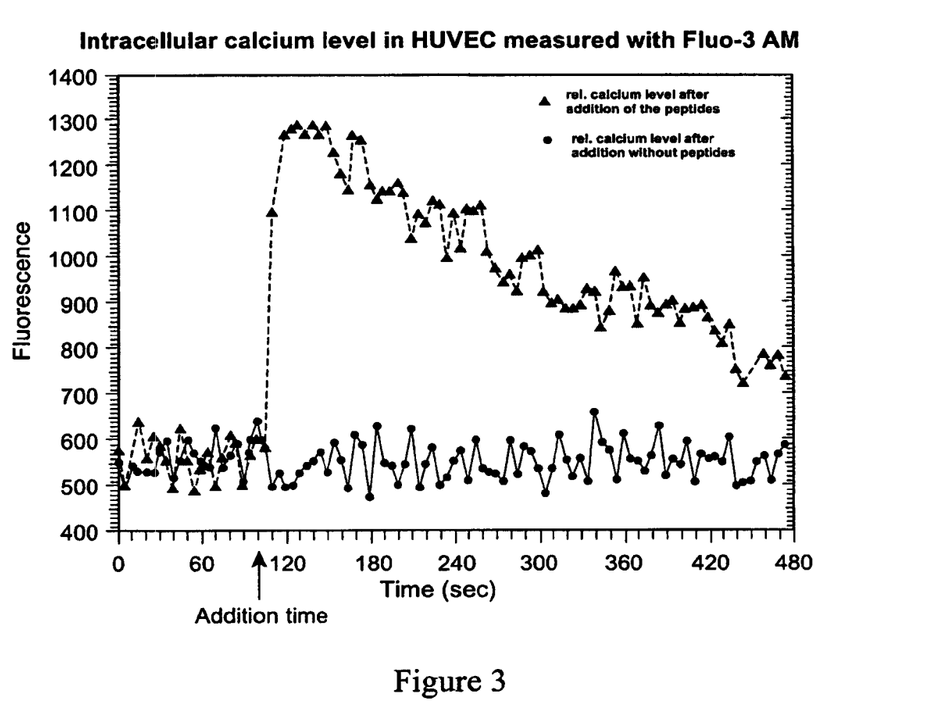
FIG. 3 shows the change in the intracellular calcium level of endothelial cells in static culture after the use of thrombospondin and the two active peptides.

Binding of TSP-1 to IAP and $\alpha_v\beta_3$ is followed by a calcium influx into the cell (FIG. 3). This calcium influx is observed immediately after addition (within a period of a few seconds) and is one step in the signal transduction which finally leads to induction of apoptosis. It is thus possible by using fluorescent calcium indicators [Merrit, J. E. et al., Biochem. J. 269, 513–519 (1990)] to set up a very quick test method for inhibition of apoptosis through the nonappearance of the calcium signal (FIG. 3, explained in detail in example 6).

Figure 4:
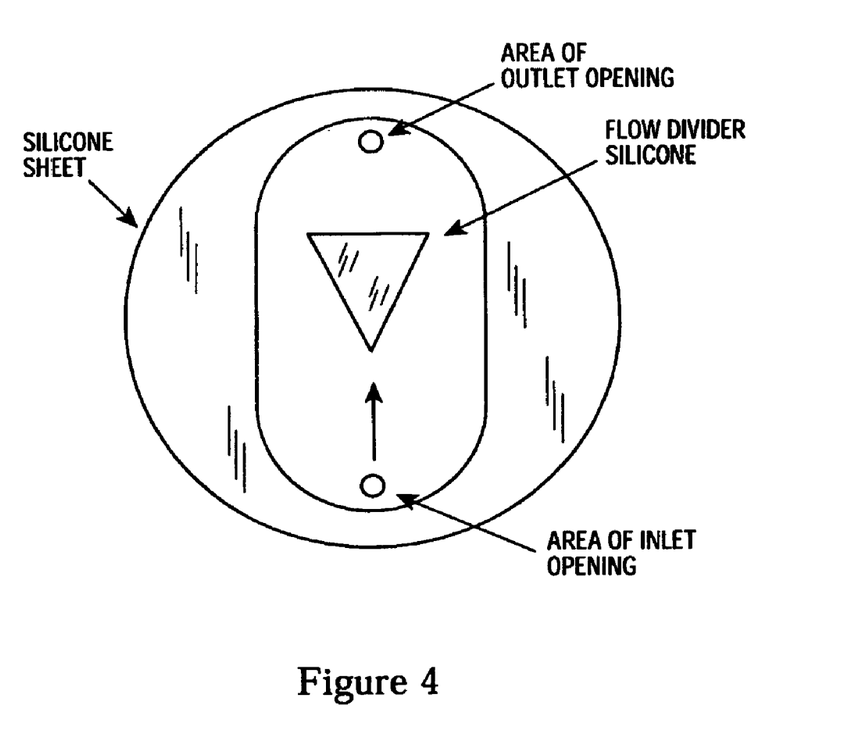
FIG. 4 shows the geometry of the flow chamber and of the flow divider in the perfusion chamber. Endothelial cells grow in the free area.

In further investigations carried out by the inventors it was possible to show not only that static culture conditions lead to induction of apoptosis in appropriate cells, but that variable or turbulent flow conditions are sufficient therefor. Introduction of an impediment into a perfusion chamber leads to variable flow profiles. One model thereof is shown in FIG. 4. A typical flow chamber is distinguished by the possibility of generating a liquid flow which is passed at defined flow rates through a flow chamber. The flow can be driven, for example, by a pump or gravity. The particular liquid is passed via suitable flexible tubing or rigid tubes through the actual chamber. In the present system, the flexible tubing is of silicone and the rigid tubes are of stainless steel. The chamber is defined by a Petri dish with a polycarbonate insert and silicone seals.

There are also other possibilities for generating a laminar flow. It is also possible to employ for this purpose other suitable apparatus, e.g. a cone and plate apparatus, in which the flow is generated by the rotation of a liquid-filled plate or the rotation of a cylindrical plug in the liquid on the plate.

Figure 5A:
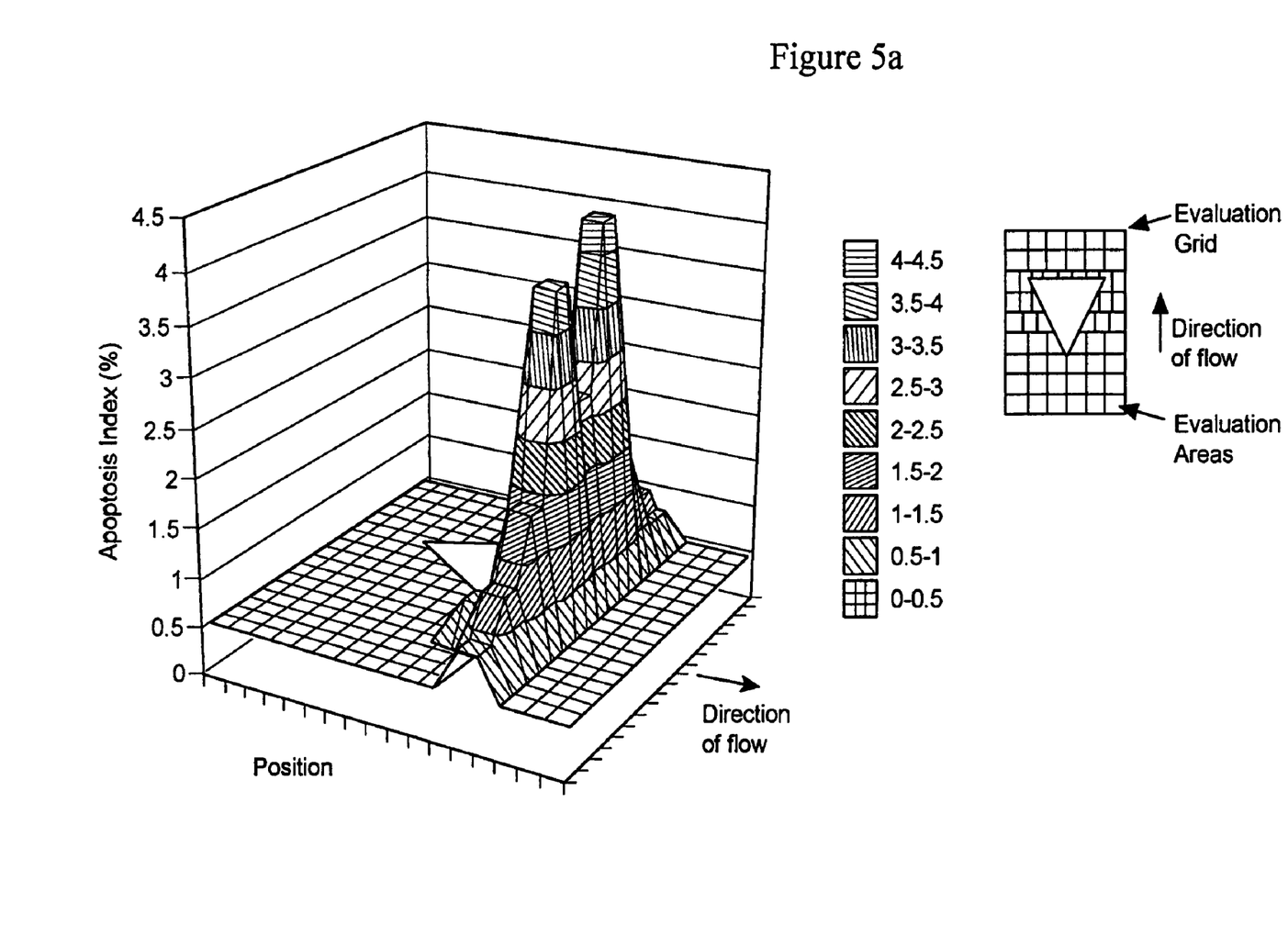
FIGS. 5a and 5b show evaluation grids for experiments with the flow divider and a position-resolved representation of the occurrence of apoptosis in the perfusion culture with variable flow conditions. After perfusion culture for 2 days, the apoptosis rate is determined for each area. Significant apoptosis rates can be detected behind the flow divider. The apoptosis rate depends on the position in the perfusion chamber.
Figure 5B:
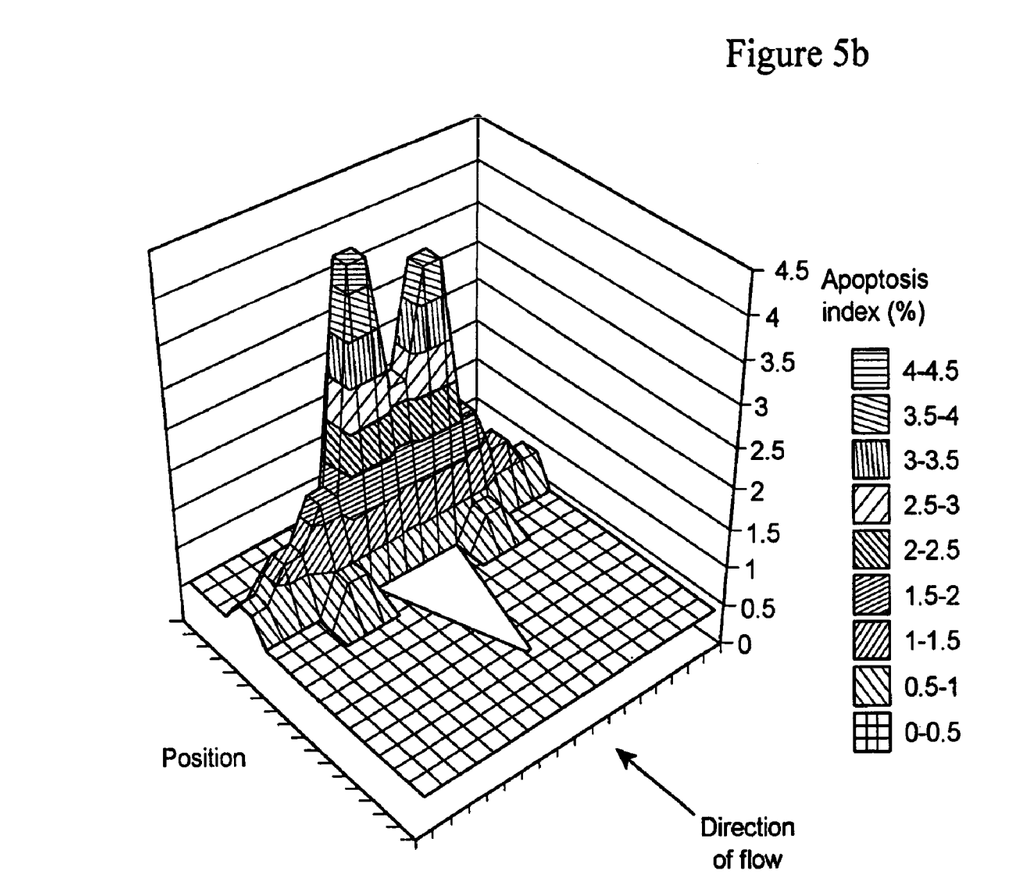

It was further possible to show for the first time by in vitro investigations that apoptosis is induced in endothelial cells exactly in the regions of variable flow profiles. It was possible to demonstrate this by a space-resolved investigation of apoptotic cells in the perfusion system (FIG. 5).

The presented results show that the actual cause of the induction of apoptosis is the absence of an invariable laminar flow. This causes the endothelial cells to secrete TSP-1, which subsequently leads, through the interaction with the integrin $\alpha_v\beta_3$ and IAP, to induction of apoptosis.

It is possible on the basis of the presented findings to develop a test method which makes a targeted search for inhibitors of the induction of apoptotic processes possible. It is thus possible to identify substances with antiapoptotic activity. For this purpose, cells which express both IAP and the integrin $\alpha_v\beta_3$ are cultured. The cells may be natural or generated by recombination. Such cells are known to the skilled worker. Preference is given in this connection to cultivated endothelial cells and, in a particularly preferred embodiment, to human umbilical vein endothelial cells (HUVEC). Further examples of suitable cells are monocytes, erythrocytes, activated T cells, fibroblasts, blood platelets, CHO cells, smooth muscle cells and ovarian tumor cells. Whole cell lines may also be suitable, such as, for example, bone marrow cell lines. The cells used in the method of the invention may also be cells which have been genetically modified so that they express recombinant IAP or integrin $\alpha_v\beta_3$, which has been modified where appropriate with retention of the original binding properties, on their cell surface.

These cells are cultivated in suitable cell culture vessels in suitable cell culture media, which are normally standard media generally known in the prior art. For example, the cells are cultivated in DMEM, M-199, IF basal media etc. Suitable culture media are now available for virtually all cells and cell lines. Growth factors and hormones such as, for example, fetal calf serum (FCS) can be added to the culture medium before starting the culture. Mammalian cells are usually cultivated at 37° C. in a 5% $CO_2$ atmosphere which, in connection with the buffers used in the cell culture media, e.g. sodium carbonate buffers, makes it possible to stabilize the pH of the cell culture medium. A further possibility is to add to the cell culture media, before starting the cultivation, antibiotics which interact specifically with prokaryotic contaminating microorganisms and inhibit their growth, but leave the growth of the eukaryotic cells virtually unaffected and thus protect the cell culture from contamination. Further hints and information for cell culturing can be found in standard works, e.g. Zell-und Gewebekultur, 3rd edition, Toni Lindl, Jörg Bauer, (1994), Gustav Fischer Verlag.

Suitable culture conditions for cultivating HUVEC and other endothelial cells are given in example 1 and example 2.

Apoptosis is then induced by the culturing conditions or by adding one or more apoptosis-inducing substances. Culturing conditions of this type are preferably those with which regular laminar flows do not occur, as explained above.

Mediators can be added to the test system in addition to or in place of the chosen flow conditions for induction or increasing the apoptosis rate. Simultaneous addition of mediators increases the sensitivity of the test system. The spontaneous apoptosis rate in a static cell culture is relatively low compared with apoptosis rates induced by mediators such as TNF-$\alpha$. The apoptosis rates reached in the tests of the spontaneous apoptosis rate induced by the static cell culture condition are in the range from 0.5 to 7% of the total cells. In the case of apoptosis induced by mediators, apoptosis rates of up to 50% may be reached.

For this reason, in the method of the invention there is addition, particularly preferably before measurement of the inhibition of the apoptosis rate by potential inhibitors, of substances which induce an increased apoptosis rate, so that the measured signal is enhanced. The added mediator preferably brings about apoptosis rates of from at least 1% up to more than 10 to 50%. This particularly preferably entails adding TSP-1 to the cell culture system, because TSP-1 is the natural mediator of apoptosis whose interaction with the IAP and $\alpha_v\beta_3$ cell receptors is to be suppressed. It is possible by adding TSP-1 to reach apoptosis rates of 5%, preferably of 7%, particularly preferably of 10%, depending on the concentration of the mediator. However, it is clear that other substances which interact with $\alpha_v\beta_3$ and IAP in an analogous manner to TSP-1 are also suitable according to the invention. An alternative to TSP-1 in the sense referred to above is to increase the apoptosis rate by simultaneous addition of the RGD and CBD peptides.

These mediators are hormones and other substances with apoptotic activity. These mediators are added in dissolved form to the cell culture, and it should be noted that the solutions used must be sterile. The sterility of the solutions can be achieved in various ways, preferably by heat treatment (autoclaving at 2 bar and 120° C.) or, if this method is unsuitable because of a particular sensitivity of the mediator to heat, by sterilizing filtration, for example using Nalgene disposable sterilizing filters. Methods of this type for sterilizing additions to cell culture are well known to the skilled worker.

To identify substances having antiapoptotic activity, test substances whose effect on the apoptosis of the cultivated cells is to be investigated are added to the cell culture. These are preferably monoclonal antibodies, antibody fragments, polyclonal antibodies and peptides. However, it is also possible to add other substances suspected of being able to display an antiapoptotic effect. These substances are preferably administered in dissolved form. The solvents must in this case be compatible with the cell culture. These test substances are therefore preferably dissolved in buffer solutions, which have generally become widely used in cell culture. Examples thereof are phosphate buffers, sodium carbonate buffers and others. The dissolved test substances are preferably sterilized by filtration (sterilized) by sterilizing filtration (Nalgene disposable sterilizing filters) before addition to the cell culture in order to remove contaminating microorganisms or spores of fungi and undissolved constituents.

The dissolved test substance is preferably equilibrated i.e. adjusted to the temperature of the cell culture, before addition to the cell culture. The volumes depend on the concentration which is to be reached of the test substance employed, and the volumes are preferably small so that no dilution effects occur in the cell culture media. The methods which can be used to introduce such test substances into cell cultures, preferably in the dissolved state, are well known to the skilled worker.

The decrease in the apoptosis rate can be determined by any suitable measurement method. A particularly suitable early indicator is measurement of the nonappearance of the calcium influx into the cell through use of intracellular calcium indicators. A method suitable for determining the exact apoptosis rates is staining of the DNA of apoptotic cells and subsequent morphometric cell nucleus analysis or analysis of the cellular DNA content in a flow cytometer. An example of a suitable fluorescent dye is DAPI. These methods are well known in the prior art and are generally used for detecting apoptotic cells. If the number of apoptotic cells decreases after the use of a potential inhibitor of apoptosis by more than 50%, preferably more than 70% and particularly preferably by more than 90%, based on the number of apoptotic cells in the test system in static culture, where appropriate after addition of an apoptosis-inducing substance, then this substance is regarded according to the invention as an inhibitor of apoptosis in the cells used. The nonappearance of the calcium influx into the cell can be used as early indicator for screening purposes. Substances which lead to a nonappearance of the calcium influx must subsequently be detected by DAPI staining.

It is also possible to use other DNA dyes (e.g. Hoechst 33258) or conventional methods such as the TUNEL assay (Tdt-mediated X-dUTP nick end labeling; DNA breaks), the detection of apoptotic enzymes (e.g. PARP, caspases) or proteins (e.g. p53, CD95), the translocation of phosphatidylserine with fluorescent annexin or the detection of the DNA ladder in an agarose gel.

It is possible with the method of the invention to find substances with antiapoptotic activity. These are preferably compounds which bind either to receptors on the cell surface, particularly preferably IAP and/or the integrin $\alpha_v\beta_3$, or to humoral factors in the blood circulation, particularly preferably TSP-1, in such a way that the specific simultaneous interaction described herein between TSP-1 and IAP and $\alpha_v\beta_3$, which leads to induction of apoptosis, does not take place, so that apoptosis cannot be induced and thus does not occur.

In a further preferred embodiment, these substances bind to IAP and thus prevent the apoptosis-specific calcium influx into the cell, so that apoptosis cannot be induced and thus does not occur.

These inhibitors are suitable for producing pharmaceutical preparations which can be used to treat conditions in which a suppression of apoptosis is desired, preferably in the vascular system for suppressing apoptosis of endothelial cells and other cells (e.g. smooth muscle cells). It is possible in principle to use the substances which have antiapoptotic activity and can be identified by the method of the invention to inhibit apoptotic states in all cells which express IAP and $\alpha_v\beta_3$ on their surface. This makes it possible to treat conditions in which an inhibition of apoptosis is indicated, such as, in particular, arteriosclerosis, which leads via inhibition of programmed cell death in the lesions to an improvement in the state of the vessels. A prophylactic treatment is also made possible by use of such inhibitors in pharmaceutical preparations.

Active substances to be tested with the method of the invention are, in particular, monoclonal antibodies and peptides which can easily be obtained with conventional methods of molecular biology and genetic manipulation. However, it is clear that other substances which have a corresponding effect can also be found using the test system of the invention. The term "antibody" is used here to describe both complete antibodies (i.e. antibodies which have two heavy and two light chains) and fragments of antibodies which have an antigen-binding site. The identification of an anti-TSP-1 antibody with antiapoptotic activity is described in example 9. It is possible in a similar way to test many other antibodies or antibody fragments in order to prevent induction of apoptosis.

It is clear that it is possible to produce a whole series of peptides and antibodies (antibody fragments) which can be identified as having antiapoptotic activity using the method of the invention in a similar way. In addition, it is also possible to identify other substances which are not antibodies (antibody fragments) or peptides as having antiapoptotic activity with the aid of the method of the invention.

Particularly preferred substances which can be investigated as test substances in the test system of the invention are low molecular weight compounds. Such compounds often have no or only a few side effects if they are employed as active principle in a pharmaceutical composition. A further advantage of such substances is the possibility of oral administration.

Examples thereof are cyclic pentapeptides as described by Haubner et. al., J. Am. Chem. Soc. 1996, 118, 7641–7472. The low molecular weight substances include according to the invention small peptides, amino acids and amino acid analogs, steroids, nucleotides and other organic chemical substances with a molecular weight of $\leq 5\,000$, preferably $\leq 3\,000$ and particularly preferably $\leq 2\,000$. [Haubner, R., Gratias, R., Diefenbach, B., Goodman, S. L., Jonczyk, A., Kessler, H., *Structural and Functional Aspects of RGD-Containing Cyclic Pentapeptides as Highly Potent and Selective Integrin $\alpha_v\beta_3$ Antagonists*, 118, 7461–7472 (1996)].

Corresponding products are produced by conventional methods. For example, it is possible to dissolve peptides or antibodies (antibody fragments), which are active ingredients of a pharmaceutical preparation, in a pharmaceutically acceptable carrier. One example of a pharmaceutically acceptable carrier may be buffer solutions such as phosphate buffer or citrate buffer. It is also possible to maintain the activity of the peptides by adding reagents which are pharmaceutically acceptable and, for example, maintain a reducing environment in the pharmaceutical preparation.

The specific dosage and posology for each patient depends on a number of factors, including the activity of the specific compounds used, the age of the patient, the body weight, the general state of health, the sex, the diet, the time of administration, the route of administration, the rate of excretion, the combination with other medicaments and the severity of the individual disorder for which the therapy is applied. It will be established by his physician as a function of these factors.

Polypeptide medicaments, e.g. protein medicaments or antibody medicaments, are normally administered parenterally, e.g. by an inhalation spray, rectally, by subcutaneous, intravenous, intramuscular, intra-articular and intrathecal injection or infusion techniques, or externally in pharmaceutical formulations which comprise conventional pharmaceutically acceptable carriers, adjuvants and vehicles. Other routes of administration are also suitable depending on the nature of the identified substance, e.g. orally.

The invention likewise provides pharmaceutical compositions which comprise an effective amount of a substance having antiapoptotic activity in combination with a conventional pharmaceutical carrier. A pharmaceutical carrier is, for example, a solid or liquid filler, an encapsulating material or a solvent. Examples of materials which can be used as pharmaceutical carriers are sugars such as lactose, glucose and sucrose; starch such as corn starch and potato starch; cellulose and derivatives thereof, such as sodium carboxymethylcellulose, ethylcellulose and cellulose cetate; powdered tragacanth; malt; gelatin; tallow; medicament carriers such as cocoa butter and suppository waxes; oils such as peanut oil, cottonseed oil, safflower oil, sesame oil, olive oil, corn oil and soybean oil; polyols such as propylene glycol, glycerol, sorbitol, mannitol and polyethylene glycol; esters such as ethyl oleate and ethyl laureate; agar; buffering agents such as magnesium hydroxide and aluminum hydroxide; alginic acid; pyrogen-free water; isotonic saline; Ringer's solution, ethyl alcohol and phosphate buffer solutions as well as other non-toxic compatible substances which are used in pharmaceutical formulations. Wetting agents, emulsifiers and glidants such as sodium lauryl sulfate and magnesium stearate, as well as coloring agents, glidants, coating agents and perfuming agents and preservatives may likewise be present in the preparations according to the requirements of the pharmaceutical technologist. The amount of active ingredient combined with the carrier materials in order to produce a single dose will vary depending on the treated patient and the specific method of administration. One example of such a pharmaceutical formulation is shown in example 10.

Abbreviations

IAP: Integrin-associated protein (CD 47)
CBD: C-terminal cell-binding domain
TSP-1: Thrombospondin 1
RGD: Arg-Gly-Asp
HUVEC: Human umbilical vein endothelial cells
HPEC: Human placental endothelial cells
DAPI: 4',6-Diamidino-2-phenylindole The following figures explain the invention in more detail:

The following examples explain the invention in more detail.

EXAMPLE 1

Cultivation of Human Endothelial Cells from Umbilical Veins (HUVEC)

Solutions (Sterile):
  Culture medium: IF basal medium+15% (v/v) NCS, 5 µg/ml transferrin, 5 µg/ml heparin, 0.7 µg/ml FGF, 2 mM L-glutamine [IF basal medium: 1:1 mixture of Iscove's modified Dulbecco medium (IMDM) and Ham's F12, both from Life Technologies, Paisley (England)]
  NCS: Newborn calf serum (Sebak, Aidenbach)
  FGF: Fibroblast growth factor (own preparation purified from pig brain)

Materials:
  Cell culture vessels, gelatinized
  HUVEC are cultivated in gelatin-coated culture vessels at 37° C., 5% $CO_2$ with a water vapor-saturated air atmosphere. The culture medium is changed every 2–3 days; at confluence, the cells are passaged with a division rate of from 1:3 to 1:5. HUVEC grow with strict contact inhibition and form monolayer cell lawns with a typical cobblestone morphology. At confluence, the cultures reach cell densities of $4-9 \times 10^4$ cells/$cm^2$. Only HUVEC cultures of passages 1–4 are used for apoptosis investigations.

Supplement

Coating of Culture Vessels

Solutions (Sterile)
  Gelatin solution, 1% (w/v) in Milli-Q water Suspend 1 g of gelatin (cell culture-tested) in 100 ml of Milli-Q water, dissolve by autoclaving at 121° C. and 2 bar for 20 min and store at room temperature.
  PBS (140 mM NaCl, 3 mM KCl, 8 mM $Na_2HPO_4$, 1.5 mM $KH_2PO_4$)
    8 g/l NaCl
    0.2 g/l KCl
    1.44 g/l $Na_2HPO_4 \times 2\ H_2O$
    0.2 g/l $KH_2PO_4$
  Dissolve the salts in an appropriate volume of Milli-Q water, autoclave at 121° C. and 2 bar for 20 min and store at room temperature. The pH is checked and is between 7.2 and 7.4.

Materials:
  Cell culture vessels

Procedure:
  Culture vessels are coated with gelatin for the cultivation of adherently growing cells. The base of the cell culture vessels is covered with sterile gelatin solution, and the cell cultures are left at room temperature for 15 min. The gelatin solution is aspirated off, the cell culture vessels are washed once with PBS and can be used thus.

Subcultivation of Adherent Cells

Solutions (Sterile)
  PBS
  Trypsin/EDTA (0.05% (w/v)/0.02% (w/v))
    0.1 ml of trypsin stock solution
    0.05 ml of EDTA stock solution
  Make up to 50 ml with sterile PDS and store in 10 ml portions at −20° C.

Materials:
  Cell culture vessels, gelatinized

Procedure:
  All the cell types listed are detached from the culture surface with trypsin/EDTA solution. The culture medium is aspirated off, the base of the culture vessel is briefly washed with PBS and covered with trypsin/EDTA solution (~1 ml for a 25 $cm^2$ culture bottle). The enzyme solution is aspirated off again immediately so that a thin film of liquid remains on the cells. The cells are left at room temperature for 1–10 min, and detachment of the cells is followed under the microscope. The detachment of the cells can be speeded up by gentle tapping of the edge of the culture vessel. The cells are taken up in fresh culture medium, possibly counted and seeded into new culture vessels.

EXAMPLE 2

Cultivation of Bovine Aorta Endothelial Cells (BAEC)

Solutions (Sterile):
Culture medium: IF basal medium+5% (v/v) NCS, 5 μg/ml transferrin, 20 μg/ml heparin, 2 mM L-glutamine; temperature adjusted to 37° C.

Materials:
Cell culture vessels, gelatinized

Procedure:
BAEC are cultivated in gelatin-coated culture vessels at 37° C., 5% $CO_2$ with a water vapor-saturated air atmosphere. The culture medium is changed every 2–3 days; at confluence, the cells are passaged with a division rate of from 1:3 to 1:5. BAEC grow with strict contact inhibition and form monolayer cell lawns with a typical cobblestone morphology. The cell density is $7–9 \times 10^4$ cells/cm$^2$.

EXAMPLE 3

Cultivation in the Perfusion System

Solutions (Sterile):
Medium (specifically for the particular cells/HUVEC, see example 1)
Milli-Q water (purified water for cell cultures)

Materials:
Small Petri dish, gelatinized
Polycarbonate plug for Petri dishes
Silicone sheets
Peek screws
Silicone tubing ID 0.5 mm
Maprene pump tubing ID 1 mm
Aluminum plate with fastenings for plug
Greiner tubes
Schott bottles with Teflon lid seal Procedure:
The cells are subcultivated as described. After the adherent cells have reached confluence, they can be introduced into the perfusion system. A system is assembled for this purpose. All the parts have previously been cleaned thoroughly with Milli-Q water. The completely assembled system is autoclaved for 40 minutes. The storage vessel consists of a Schott bottle with a special Teflon lid. The lid has 3 holes through which stainless steel tubes (3 cm, 1 mm ID) are passed. One tube is provided with a sterilizing filter and serves for pressure equalization. The other two form the inlet and outlet for the medium. One tube is extended toward the inside with silicone tubing so that it dips into the medium in the bottle. From here, it continues through silicone and Maprene pump tubing to a 15 ml Greiner tube which is likewise closed with a special Teflon lid through which in turn two stainless steel tubes pass. The Greiner tube serves for preheating the medium and as an air bubble trap. From here, the medium is passed through further silicone tubing to the plug and to the Peek connector on the upper side of the plug. For the cultivation, the plug is placed on a Petri dish with the relevant cells. The plug is sealed by an O ring on the side. A specially cut silicone sheet is placed on the base of the Petri dish to prevent crushing of the cells. The exit from the plug is in turn coupled by means of a Peek adapter to silicone tubing and returns the medium to the medium reservoir. Before starting the system, the medium storage vessel and the Greiner tube are charged with preheated medium. The medium in the Petri dish is aspirated off from the cells, and the silicone sheets are cautiously placed inside. The plug is then rapidly pressed on, and the system can be attached to the peristaltic pump. The pumping rate can be adapted according to the requirements of the cells. It depends on the internal diameter of the pump tubing and the chosen pump revolution count. After a perfusion time which can be chosen unrestrictedly, the system can be disassembled in a sterile cabinet, and the cells can be employed for further tests. The modular design makes diverse uses of the system possible. It is possible with the aid of valves and switches from HPLC technology for substances to be introduced subsequently and for samples of medium to be removed. It is also possible by using adapted medium (e.g. IF medium with 25 mM HEPES buffer, 12.5 mM NaCl and 0.5 mM sodium carbonate) to work outside an incubator. A hotplate or a heated chamber is then used for temperature control.

For the experiments with the flow divider, a further silicone sheet is also placed inside (cf. FIG. 4). It is possible in this way to change the flow characteristics in the chamber.

EXAMPLE 4

Cultivation in the Cone and Plate Shear Apparatus

Solutions:
Culture medium with 200 U/ml penicillin, 200 μg/ml streptomycin
70% (v/v) ethanol Material:
Cone and plate shear apparatus, Bussolori et al. (1982) Rev. Sci. Instrum. 53, 1851–1854.
Gelatinized culture dish (Ø=94 mm)

Procedure:
The cone and plate shear apparatus is first cleaned with a soft cloth and 70% ethanol, the cone is sterilized, and the apparatus is then stabilized at 37° C. in a heating cabinet for at least 30 min. The precultivated cells are washed with culture medium and provided with 0.06 ml/cm$^2$ fresh culture medium, and the culture dish is rapidly fitted into the cone and plate shear apparatus.

The cone is raised using the coarse adjustment, and the culture dish together with lid is carefully inserted into the holder provided therefor. The lid is taken off and the cone is lowered onto the culture dish and adjusted: the tip of a cone is then a minimal distance from the cell lawn and the cone moves round without abrading. The assembled cone and plate shear apparatus is placed in an incubator at 37° C., 5% (v/v) $CO_2$ with a water vapor-saturated atmosphere for dynamic cultivation of the cells.

EXAMPLE 5

Preparation of Conditioned Medium

Solutions (Sterile):
HUVEC medium

Materials:
HUVEC, confluent
Greiner tubes

Procedure:
HUVEC culture medium from example 1 is brought onto a confluent cell lawn of human umbilical vein endothelial cells and conditioned for 48 hours–72 hours. The conditioned medium is then centrifuged at 1 000×g for 5 minutes. The conditioned medium is frozen at −20° C. until used. The conditioned HUVEC medium is employed for apoptosis investigations. For this purpose it can be supplemented with 2 mM glutamine and 0.7 µg/ml FGF.

EXAMPLE 6

Determination of the Apoptosis Rate by Staining of Apoptotic Cells with DAPI

DAPI belongs to the group of indole dyes and is a selective DNA dye. The dye is excited at 340–360 nm, and the emission maximum is at 480 nm. It is employed for apoptosis investigations [cf. Cohen et al., Immunology Today, 14, No. 3, 126–130 (1993)].

Morphological Evaluation:

Solutions:
  PBS
  Formaldehyde solution
    4% (v/v) formaldehyde in PBS
  DAPI solution (Molecular Probes, Leiden, The Netherlands)
    2 µg/ml DAPI in metanol Materials:
  Petri dish (35 mm) with cells in culture Procedure:
  The culture supernatant is aspirated off of a Petri dish, and the cell lawn is fixed with 1 ml of formaldehyde solution on ice for 15 minutes, washed twice with 2 ml of PBS, treated with 0.5 ml of DAPI solution for 15 minutes, washed with PBS and evaluated under a fluorescence microscope. The UV filter set and a 20× or 40× objective are used. 500–1 000 cells are selected at random, and the cells with apoptotic nuclei are counted.
  The apoptosis index is calculated by the following formula:

$$\text{Apoptosis index [\%]} = \frac{\text{number of apoptotic cells}}{\text{total number of cells}} \cdot 100$$

Flow Cytometry:

Solutions:
  PBS
  Medium
  Ethanol (analytical reagent ice-cooled (−20° C.)
  DAPI buffer
  DAPI stock solution
  DAPI stain solution Procedure:
  The culture supernatant is aspirated off, and the cells are trypsinized without being washed with PBS. The cell suspension is taken up in medium, counted and centrifuged at 800×g for 5 minutes, and the sediment is resuspended in 0.5 ml of IF and added dropwise to 1.5 ml of ice-cold ethanol. The suspension is stored at −20° C. overnight. Renewed centrifugation and resuspension of the sediment in 2 ml of PBS are followed by incubation at 37° C. for half an hour, a further centrifugation, resuspension of the sediment in 5 ml of DAPI solution and counting in a flow cytometer at a counting rate of 50–300 events per second. The resulting plot shows a large peak of cells in the $G_1$ phase of the cell cycle, followed by a fraction of cells in the S phase (medium fluorescence intensities) and a last peak of high fluorescence intensities, which represents the cells in the $G_2$ phase. Apoptotic cells appear, owing to the decreasing absolute amount of DNA per cell, in a sub-$G_1$ peak [Darzynklewicz Z. et al., Cytometry, 13, 795–808 (1992); Zamai L. et al., Cytometry, 14, 891–897 (1993)]. This shows the occurrence of apoptosis under the chosen conditions.

EXAMPLE 7

Measurement of the Induced Calcium Influx into the Cells Through Use of the Intracellular Calcium Indicator Fluo-3 AM Fluo-3 is a calcium indicator which forms a fluorescent complex after binding of $Ca^{2+}$. The ester Fluo-3 AM is taken up by the cells through diffusion. The calcium indicator Fluo 3 is produced only after hydrolysis of the ester in the cell. Extracellular dye ester thus does not impair the measurement. The measurement is carried out with normal fluorescein filters. At an excitation wavelength of 488 nm (500 nm), the emission maximum is at 525 nm and increases by a factor of 100 (200) through calcium binding. The measurement range is between 0.05 and 20 µM free $Ca^{2+}$ (Merritt, J. E. et al., *Biochem. J.* 269, 513–519 (1990).

Solutions:
  PBS
  Medium
  Fluo-3 AM stock solution
    50 µg in 10 µl of DMSO dimethyl sulfoxide (Molecular Probes, Leiden) (6 mM)
  Fluo-3 AM concentration used
    3 µM in serum-free medium Materials:
  Cells in culture Procedure:
  Confluent HUVEC cell lawns in 24-well plates are washed three times with serum-free medium, incubated with preheated serum-free medium with Fluo-3 AM under culture conditions for 30 minutes and washed three times, and the plate is measured with a fluorimeter. First the sensitivity of the instrument is adjusted, and then fluorescence values corresponding to the instantaneous calcium level in the cell are recorded every 1–10 seconds. Substances can be added to the cells while the measurement is taking place. If a substance has an effect on the calcium level, this can be recognized from the increase or decrease in the fluorescence values (see FIG. 3). Assessment of the calcium level is possible with this method. The calcium influx is an early sign of apoptosis taking place.

EXAMPLE 8

Induction of Apoptosis in Cultivated Endothelial Cells with TSP-1

The cells are cultivated as described in examples 1 and 2. After complete confluence is reached, the cells are employed for the test. Firstly, thrombospondin 1 is added in various concentrations (1–600 µg/ml) to fresh medium and compared with the effect of conditioned medium on the spontaneous apoptosis rate of HUVEC. The following table shows that addition of thrombospondin leads to a significant increase in the apoptosis rate. It corresponds to that achievable with conditioned medium. The apoptosis observed on addition of fresh medium is induced by the thrombospondin secreted during the experiment. Thrombospondin has no effect on perfused HUVEC. The apoptosis rate is determined by staining apoptotic cells with DAPI.

TABLE 3

| Culturing conditions | Culture medium | Apoptosis rate (%) after 24 h |
|---|---|---|
| Static | Fresh medium | 0.9 ± 0.1 |
| Static | Conditioned medium | 3.0 ± 0.2 |
| Static | Fresh + TSP-1 (1 µg/ml) | 3.0 ± 0.4 |
| Dynamic | Fresh medium | <0.1 |
| Dynamic | Conditioned medium | <0.1 |
| Dynamic | Fresh + TSP-1 (1 µg/ml) | <0.1 |

The apoptosis rate has been indicated after DAPI staining as shown in example 5 (the mean and the standard deviation in each case are indicated). The percentage apoptosis rate is based on the total cell count.

EXAMPLE 9

Test System for Peptides or Proteins with Antiapoptotic Activity

The cells are cultivated as described in examples 1 and 2. The cells are seeded into the appropriate culture vessels (e.g. 24-well plate/0.5 ml per well) and employed for the test after complete confluence is reached. Investigations into the effect of various peptides and proteins (table 2) on the apoptosis rate of endothelial cells are carried out. For this purpose, the peptides and proteins (table 2a) are dissolved in culture medium (example 1) and employed in the stated concentrations (table 2a). The medium with the dissolved samples is added to the cells and incubated under culture conditions (example 1) for three days. The cells are then stained with DAPI to determine the apoptosis rate as described in example 5. The results of 3 independent experiments are compiled in table 2, stating the means and the standard deviation. The apoptosis-inducing effect of conditioned medium, TSP-1 and of active RGD peptide together with the CBD peptide is clearly evident.

Intracellular calcium measurement (example 6) can be employed as early indicator. For this purpose, the cells are first pretreated as described in example 6 and measured in a fluorimeter at the time of addition of the peptides or of TSP-1. Only TSP-1 or simultaneous addition of both peptides leads to an increase in the intracellular calcium level (FIG. 3). The addition of fresh medium or of only one peptide has no effect on the calcium level. The influx of calcium into the cells can be employed as early indicator. Verification of positive substances (calcium signal) can be obtained by determining the apoptosis rate with DAPI (example 5) after incubation for at least 24 hours. It is thus possible to identify compounds with antiapoptotic activity rapidly and unambiguously.

TABLE 4

| Ligand | Concentration | Incubation time | Biological activity |
|---|---|---|---|
| Thrombospondin | 1 µg/ml | (2−) 24–72 h | binds integrin $\alpha_v\beta_3$ and IAP |

TABLE 4-continued

| Ligand | Concentration | Incubation time | Biological activity |
|---|---|---|---|
| RGD cyclic, act. | 250 µg/ml | (2−) 24–72 h | binds integrin $\alpha_v\beta_3$ |
| RGD cyclic, inact. | 250 µg/ml | (2−) 24–72 h | Inactive |
| IAP peptide (CBD) | 400 µg/ml | (2−) 24–72 h | binds IAP |

EXAMPLE 10

Identification of an Antibody with Antiapoptotic Activity Using the Method of the Invention The cells are cultivated as described in examples 1 and 2. The cells are seeded in the appropriate culture vessels (e.g. 24-well plate/0.5 ml per well) and employed for the test after complete confluence is reached. The cells are supplied with new medium: (a) fresh culture medium [basic apoptosis rate], (b) conditioned medium (example 4) [apoptosis-inducing ffect], (c) conditioned medium with rabbit anti-TSP-1 antiserum (1:20) [apoptosis-inducing and apoptosis-inhibiting substances], (d) fresh culture medium with rabbit anti-TSP-1 antiserum (1:20) [apoptosis-inhibiting substance], (e) fresh medium with 1 µg/ml TSP-1 [apoptosis-inducing substance], (f) fresh medium with 1 µg/ml TSP-1 and rabbit anti-TSP-1 antiserum (1:20) [apoptosis-inducing and apoptosis-inhibiting substances], (g) fresh medium with monoclonal anti-TSP-1 antibody (1:30) [apoptosis-inhibiting substance]. After incubation under culture conditions (example 1) for 24 h, the cells are fixed, stained with DAPI and examined morphologically under a fluorescence microscope or investigated by flow cytometry (example 5). The apoptotic cells and the total cell count are determined and the apoptosis index is calculated (percent of apoptotic cells). The data of 3 independent experiments are indicated in table 3, stating the mean and standard deviation.

The experiments with polyclonal antiserum (=antiserum: polyclonal antibody against TSP-1 (from rabbits) unpurified; protein concentration: 900 µg/ml) and with a monoclonal antibody against TSP-1 (=mAb: monoclonal antibody against TSP-1 M 101 unpurified; protein concentration: 300 µg/ml) show a significant decrease in the apoptosis rate (>50%) and can be employed as inhibitors of natural apoptosis-inducing substances (conditioned medium and TSP-1). It was thus possible to identify them as antiapoptotic. The antiserum and the monoclonal antibody were provided by Prof. P. Vischer, Institut für Arterioskleroseforschung Münster.

The test system can also be carried out with the calcium indicator Fluo-3 AM. For this purpose, the cells are likewise cultivated as described in examples 1 and 2. The cells are employed for the test after complete confluence is reached. They are loaded with a calcium indicator (example 6) placed in a fluorimeter and measured. During the measurement, the substances b, c, e, f, g are added to the cells. An activator (conditioned medium or TSP-1) is present in each of these examples. In examples b) and e) there is an influx of calcium and thus an increase in the measured fluorescence values. If apoptosis-inducing substances are added at the same time, as in example c), f) and g), no increase can be observed. The monoclonal antibody against TSP-1 or the polyclonal antiserum prevent the influx of calcium and the induction of apoptosis. It is thus possible by simultaneous addition of an activator (e.g. TSP-1) and of the substance to be tested to establish a rapid test method for potential apoptosis inhibitors.

Two further antibodies which can be employed as apoptosis inhibitors were identified with this method with the described method. These are:

1. Monoclonal antibody against integrin $\alpha_v$ supplied by Chemicon (No. MAB 1960), clone VNR 139 (100 µl); dilution employed: 1:100 (mAb/$\alpha_v$)
2. Monoclonal antibody against human IAP (CD 47) supplied by CYMBUS Biotechnology (No. CBL 489), clone BRIC 126, concentration: 100 µg/ml; dilution employed: 1:100 (1 µg/ml) (mAb/IAP)

The antibodies were added to the cells after confluence was reached with the activator TSP-1 (1 µg/ml) in the stated concentrations. After incubation under static conditions for 48 hours, the following apoptosis rates were measured:

TABLE 1

| Culture medium | Apoptosis rate [%] (with SEM) |
| --- | --- |
| Fresh medium + TSP-1 | 7.3 ± 0.6 |
| Fresh medium + TSP-1 + mAb/a$_v$ | 0.9 ± 0.2 |
| Fresh medium + TSP-1 + mAb/IAP | 0.5 ± 0.1 |

| Culture conditions | Culture medium (24 h) | Apoptosis rate (%) |
| --- | --- | --- |
| Static | Fresh medium (a) | 0.9 ± 0.1 |
| Static | Conditioned medium (b) | 3.0 ± 0.2 |
| Static | Conditioned + anti-TSP 1 (c) | 0.1 ± 0.1 |
| Static | Fresh + TSP 1 (e) | 3.0 ± 0.4 |
| Static | Fresh + anti-TSP 1 (d) | 0.2 ± 0.1 |
| Static | Fresh + TSP I + anti-TSP 1 (f) | 0.2 ± 0.1 |
| Static | Fresh + mAb TSP 1 (g) | 0.4 ± 0.1 |

EXAMPLE 11

Suppression of the Apoptosis Induced by Static Culture Conditions Through Complexation of the Calcium or Inhibition of the Calcium Influx Material (In Addition to Example 1):
Culture medium with 2.5 mmol/l EGTA Procedure:
The cells are prepared as described in example 1 and, after confluence is reached, cultivated in the cone and plate shear apparatus (see example 4) for a further 24 hours. The culture dish is removed and divided into 12 independent culture wells (culture area of each well 0.8 cm²) by putting in a suitable insert. Half of the culture is cultivated in culture medium with EGTA and the second half is cultivated in culture medium without EGTA. Table 1 below shows that the result of cultivation in culture medium with EGTA is a significant reduction in the apoptosis rate, i.e. complexation of the calcium with EGTA leads to an inhibition of apoptosis. The apoptosis rate is determined by staining the apoptotic cells with DAPI.

TABLE 5

| Duration of experiment [hours] | Apoptosis rate (%) with EGTA [2.5 mM] | Apoptosis rate (%) without EGTA |
| --- | --- | --- |
| 0 | 0.40 ± 0.22 | 0.42 ± 0.23 |
| 2 | 0.42 ± 0.22 | 2.22 ± 0.55 |

TABLE 5-continued

| Duration of experiment [hours] | Apoptosis rate (%) with EGTA [2.5 mM] | Apoptosis rate (%) without EGTA |
| --- | --- | --- |
| 3 | 0.96 ± 0.27 | 2.80 ± 0.64 |
| 4 | 1.56 ± 0.23 | 3.10 ± 0.31 |
| 5 | 2.26 ± 0.35 | 5.33 ± 0.59 |

The apoptosis rate was found by the method of DAPI staining as shown in example 5 of the main patent (the mean and the standard deviation are indicated in each case). The percentage apoptosis rate is based on the total cell count.

EXAMPLE 12

Suppression of the Apoptosis Induced by the Biologically Active Peptides Through Complexation of the Calcium Material (In Addition to Example 4):
Culture medium with biologically active peptides (compare main patent example 8, table 2a)

Procedure:
The cells are prepared as described in example 1 and, after complete confluence is reached, cultivated in the cone and plate shear apparatus (see example 4) for a further 24 hours. The culture dish is removed from the shear apparatus and divided into 12 independent culture wells by putting in a suitable insert as already described in example 11. The biologically active peptides are dissolved on the one hand in culture medium with 0.5 mM EGTA and on the other hand in culture medium without EGTA (concentrations: RGD peptide: 250 µg/ml [0.5 mM]; IAP peptide: 400 µg/ml [0.5 mM]). Thereafter half of the samples is treated with culture medium with EGTA and the active peptides and the other half is treated with culture medium which contains the active peptides but no EGTA. The result of these investigations is shown in table 2 below:

TABLE 6

| Duration of experiments [hours] | Apoptosis rate (%) with EGTA and with peptides | Apoptosis rate (%) without EGTA and with peptides |
| --- | --- | --- |
| 0 | 0.45 ± 0.24 | 0.61 ± 0.22 |
| 2 | 1.00 ± 0.29 | 2.08 ± 0.22 |
| 3 | 0.65 ± 0.24 | 2.67 ± 0.18 |
| 4 | 1.25 ± 0.33 | 3.82 ± 0.50 |

Addition of the biologically active peptides in a culture medium without EGTA leads to a marked increase in apoptosis over the period of the experiment. Addition of EGTA in the culture medium with the active peptides makes it possible to achieve a significant reduction in the apoptosis rate.

The apoptosis rate was found by the method of DAPI staining as shown in example 5 of the main patent (the mean and the standard deviation are indicated in each case). The percentage apoptosis rate is based on the total cell count.

EXAMPLE 13

Use of Antibodies or Peptides as Active Substance in Pharmaceutical formulation The compounds with antiapoptotic activity identified in example 9, i.e. the anti-TSP-1 antibody, the monoclonal antibody VNR 139 and the monoclonal antibody BRIC 126, might be employed as active substances n pharmaceutical formulations.

These antibodies are for this purpose expediently employed in a concentration of 3–5 mg per ml in the following formulation:

Water for injections
Polysorbate 80
Disodium hydrogen phosphate/sodium dihydrogen phosphate
Sodium chloride This formulation is administered as solution for injection.

The invention claimed is:

1. A method for identifying test substances with antiapoptotic activity, comprising
    i) culturing cells selected from the group consisting of endothelial cells, smooth muscle cells, and fibroblasts which express both CD47 and the integrin $\alpha_v\beta_3$,
    ii) causing the cells to produce an apoptosis-inducing substance by culturing under static or turbulent flow conditions, and/or adding a substance which simultaneously binds CD47 and $\alpha_v\beta_3$, thereby inducing apoptosis,
    iii) adding a test substance, and
    iv) determining a change in apoptosis rate by determining the portion of cells with apoptotic nuclei by one of DAPI staining, tunnel assay, DNA ladder, annexin staining, or measuring increased calcium influx into the cells,
    wherein a decrease in apoptosis rate in step iy) is indicative of the test substance having antiapoptotic activity.

2. A method as claimed in claim 1, where the cells are genetically modified cells which express CD47 and $\alpha_v\beta_3$ on their surface.

3. A method as claimed in claim 1, wherein the cells are endothelial cells, comprising cultivating the endothelial cells under conditions under which consistently directed laminar flows do not occur.

4. A method as claimed in claim 1, comprising adding TSP-1 in step ii).

5. A method as claimed in claim 1, comprising determining the induction of apoptosis by measuring increased calcium influx into the cell.

6. A method as claimed in claim 1, wherein said substance which simultaneously binds CD47 and $\alpha_v\beta_3$ comprises TSP-1.

* * * * *